United States Patent
Weng

(10) Patent No.: US 7,541,578 B2
(45) Date of Patent: Jun. 2, 2009

(54) MICROFLUIDIC DEVICE AND MANUFACTURING METHOD THEREOF

(75) Inventor: Kuo-Yao Weng, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 224 days.

(21) Appl. No.: 11/614,956

(22) Filed: Dec. 21, 2006

(65) Prior Publication Data
US 2007/0145263 A1    Jun. 28, 2007

Related U.S. Application Data

(60) Provisional application No. 60/753,824, filed on Dec. 23, 2005.

(30) Foreign Application Priority Data
Jan. 18, 2006    (TW) ................. 95101886 A

(51) Int. Cl.
B01L 3/02    (2006.01)
H01J 49/04    (2006.01)

(52) U.S. Cl. .............. 250/288; 250/281; 250/282; 73/864.81; 73/864.83; 435/288.2; 239/695; 29/890.142; 264/164

(58) Field of Classification Search ............ 250/281, 250/280, 282, 423 R, 288; 73/864.81, 864.83; 264/164; 435/288.2; 239/695; 29/890.142
See application file for complete search history.

(56) References Cited

U.S. PATENT DOCUMENTS

| 4,600,424 A | * | 7/1986 | Flaming ............ 65/29.17 |
| 5,145,565 A |   | 9/1992 | Kater et al. |
| 5,788,166 A | * | 8/1998 | Valaskovic et al. ........ 239/708 |
| 5,969,353 A | * | 10/1999 | Hsieh ................ 250/288 |
| 5,994,696 A |   | 11/1999 | Tai et al. |

(Continued)

FOREIGN PATENT DOCUMENTS

WO    0030167    5/2000

(Continued)

OTHER PUBLICATIONS

Article Titled "A Microfabricated Device for Rapid Protein Identification by Microelectrospray Ion Trap Mass Spectrometry" jointly authored by Figeys et al., Analytical Chemistry, vol. 69, No. 16, Aug. 15, 1997.(pp. 3153-3160).

(Continued)

*Primary Examiner*—Jack I Berman
*Assistant Examiner*—Nicole Ippolito Rausch
(74) *Attorney, Agent, or Firm*—Jianq Chyun IP Office

(57) ABSTRACT

A method of manufacturing a microfluidic device is described. A substrate having at least one device thereon is provided, wherein the device includes at least one channel. Next, a region beside the channel is heated, and then the substrate is pulled to neck the region such that at least one capillary connecting with the channel is formed. The present invention also provides a microfluidic device including a substrate and at least one capillary. In particular, the substrate has at least one device thereon, and the device has at least one channel. The capillary is connected with the channel, wherein the substrate and the capillary are a unity structure such that the interface between the capillary and the channel is dead-volume free.

20 Claims, 9 Drawing Sheets

U.S. PATENT DOCUMENTS

| | | | |
|---|---|---|---|
| 6,417,510 | B2 | 7/2002 | Moon et al. |
| 6,459,080 | B1 | 10/2002 | Yin et al. |
| 6,673,253 | B2 | 1/2004 | Moon et al. |
| 6,723,984 | B1 | 4/2004 | McMurtry et al. |
| 6,766,817 | B2 | 7/2004 | da Silva |
| 6,800,202 | B2 | 10/2004 | Moon et al. |
| 6,800,849 | B2 * | 10/2004 | Staats .................. 250/288 |
| 6,818,157 | B2 * | 11/2004 | Kobayashi et al. ........... 264/1.6 |
| 6,858,842 | B2 | 2/2005 | Moon et al. |
| 7,297,943 | B2 * | 11/2007 | Tai et al. ................ 250/288 |
| 2004/0036019 | A1 * | 2/2004 | Goodley et al. .......... 250/288 |
| 2004/0067578 | A1 * | 4/2004 | Axelsson ............. 435/287.2 |
| 2004/0206399 | A1 * | 10/2004 | Heller et al. ............ 137/375 |

FOREIGN PATENT DOCUMENTS

| | | | |
|---|---|---|---|
| WO | WO 2006/049333 | * | 5/2006 |

OTHER PUBLICATIONS

Article Titled "Microfabricated Devices for Capillary Electrophoresis-Electrospray Mass Spectrometry" jointly authored by Zhang et al., Analytical Chemistry, vol. 71, No. 15, Aug. 1, 1999.(pp. 3258-3264).

Article Titled "Microfluidic Devices Connected to Fused-Silica Capillaries with Minimal Dead Volume" jointly authored by Bings et al., Analytical Chemistry, vol. 71, No. 15, Aug. 1, 1999.(pp. 3292-3296).

Article Titled "Development of Multichannel devices with an Array of Electrospray tips for High-Throughput Mass Spectrometry" jointly authored by Liu et al., Analytical Chemistry, vol. 72, No. 14, Jul. 15, 2000.(pp. 3303-3310).

Article Titled "Polymer Microspray with an Integrated Thick-Film Microelectrode" jointly authored by Rohner et al., Analytical Chemistry, vol. 73, No. 22, Nov. 15, 2001.(pp. 5353-5357).

Article Titled "Microfabrication of polydimethylsiloxane electrospray ionization emitters" jointly authored by Kim et al., Journal of Chromatography A, 924(2001) pp. 137-145.

Article Titled "An Electrospray Ionization Source for Integration with Microfluidics" jointly authored by Kameoka et al., Analytical Chemistry, vol. 74, No. 22, Nov. 15, 2002.(pp. 5897-5901).

Article Titled "A Fully Integrated Monolithic Microchip Electrospray Device for Mass Spectrometry" jointly authored by Schultz et al., Analytical Chemistry, vol. 72, No. 17, Sep. 1, 2000.(pp. 4058-4063).

Article Titled "Polymer-Based Electrospray Chips for Mass Spectrometry" jointly authored by Wang et al., the 12th IEEE International Conference on Micro Electro Mechanical Systems (MEMS '99), Orlando, Florida, 1999, pp. 523-528.

Article Titled "A planar on-chip micro-nib interface for NanoESI-MS microfluidic applications" jointly authored by Arscott et al., Journal of Micromechanics and Microengineering, 14(2004) 310-316.

Article Titled "Minimal dead-volume connectors for microfluidics using PDMS casting techniques" jointly authored by Chiou et al., Journal of Micromechanics And Microengineering, 14(2004) 1484-1490.

Article Titled "Microfabricated polymer injector for direct mass spectrometry coupling" jointly authored by Gobry et al., Proteomics 2002, 2, 405-412.

* cited by examiner (A)

(B)

(C)

(D)

MICROFLUIDIC DEVICE AND MANUFACTURING METHOD THEREOF

CROSS-REFERENCE TO RELATED APPLICATION

This application claims the priority benefit of U.S.A. provisional application Ser. No. 60753824, filed on Dec. 23, 2005, all disclosures are incorporated therewith. This application also claims the priority of Taiwan application serial no. 95101886, filed Jan. 18, 2006. All disclosure of the Taiwan application is incorporated herein by reference.

BACKGROUND OF THE INVENTION

1. Field of the Invention

The present invention generally relates to a microfluidic device and a manufacturing method thereof. More particularly, the present invention relates to a microfluidic device with at least a capillary having dead-volume free interface therebetween.

2. Description of Related Art

Since the concept of miniaturized total analysis systems are developed, a great number of microfluidic devices have been demonstrated for a variety of applications. Common analytical assays including polymerase chain reaction (PCR), DNA analyses and sequencing, protein separations, immunoassay, and intra- and inter-cellular analysis have been reduced in size and fabricated in a chip. The reduction in the size of the analytical processes has many advantages including rapid analysis, less sample amount, and smaller size.

Although there have been many successes, an important hurdle that still needs to be cleared is the connection between the micro-components of a device and the macro-environment of the world. This part of the device is often referred to as the macro-to micro interface. The difficulty results from the fact that samples and reagents are typically transferred in quantities of microliters to milliliters whereas microfluidic devices consume only nanoliters or picoliters of samples due to the size of reaction chambers and channels, which have dimensions on the order of microns.

Electrospray mass spectrometry is usually used to analyze or identify proteins or DNAs. The method for linking a microchip device and an electrospray tip, such as a fused silica capillary, has been disclosed in several prior art references. For example, "A Microfabricated Device for Rapid Protein Identification by Microelectrospray Ion Trap Mass Spectrometry", Anal. Chem., 1997, 69, 3153-3160; "Microfabricated Devices for Capillary Electrophoresis-Electrospray Mass Spectrometry", Anal. Chem., 1999, 71, 3258-Volume", Anal. Chem., 1999, 71, 3292-3296; "Development of Multichannel Devices with an Array of Electrospray Tips for High-Throughput Mass Spectrometry", Anal. Chem., 2000, 72, 3303-3310. In the references, a dead-volume interface will be formed between the electrospray tip and the microchip device after connecting or linking the electrospray tip to the microchip device.

In order to resolve the problem of dead-volume interface between the electrospray tip and the microchip device, some methods are provided in several prior art references, such as "Polymer Microspray with an Integrated Thick-Film Microelectrode", Anal. Chem., 2001, 73, 5353-5357; "Microfabricated polymer injector for direct mass spectrometry coupling", Proteomics 2002, 2, 405-412; "Microfabrication of polydimethylsiloxane electrospray ionization emitters", Journal of Chromatography A, 924 (2001) 137-145; "An Electrospray Ionization Source for Integration with Microfluidics", Anal. Chem., 2002, 74, 5897-5901; "A Fully Integrated Monolithic Microchip Electrospray Device for Mass Spectrometry", Anal. Chem., 2000, 72, 4058-4063; "A Fully Integrated Monolithic Microchip Electrospray Device for Mass Spectrometry", Anal. Chem., 2000, 72, 4058-4063; "Polymer-based electrospray chips for mass spectrometry", The 12th IEEE International Conference on Micro Electro Mechanical Systems (MEMS '99), Orlando, Fla., 1999, pp. 523-528 (it is also filed a patent of WO00/30167); "A planar on-chip micro-nib interface for NanoESI-MS microfluidic applications", J. Micromech. Microeng. 14 (2004) 310-316; and "Minimal dead-volume connectors for microfluidics using PDMS casting techniques", J. Micromech. Microeng., 14 (2004) 1484-1490. However, these methods disclosed in the above prior references have disadvantages of complex, time consuming and high cost.

In addition, the methods described about the micro-fabricated electrospray and electrospray nozzle have been disclosed in U.S. Pat. Nos. 5,994,696, 6,459,080, 6,417,510, 6,858,842, 6,800,202, 6,723,984, 6,673,253, WO 00/30167 and U.S. Pat. No. 5,145,565, the teachings of which are incorporated herein by reference.

SUMMARY OF THE INVENTION

Accordingly, the present invention is directed to a microfluidic device capable of resolving the problem of dead-volume existing at the interface between the microfluidic device and the electrospray tip in the prior art.

The present invention is directed to a method of manufacturing a microfluidic device having advantages of easy to manufacture, low time-consuming and low cost.

The present invention provides a method of manufacturing a microfluidic device. A substrate having at least one device thereon is provided, wherein the device comprises at least one channel. Next, a region beside the channel is heated, and then the substrate is pulled to elongate the region such that at least one capillary connecting with the channel is formed.

The present invention also provides a microfluidic device comprising a substrate and at least one capillary. In particular, the substrate has at least one device thereon, and the device comprises at least one channel. The capillary is connected with the channel, wherein the substrate and the capillary are a unity structure such that the interface between the capillary and the channel is dead-volume free.

In the microfluidic device of the present invention, the capillary and the substrate are a unity structure such that the interface between the capillary and the channel is dead-volume free. In addition, the capillary of the microfluidic device is formed with a heating and pulling step, and thus the method is simple, fast and low cost, and it is easy to mass produce.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
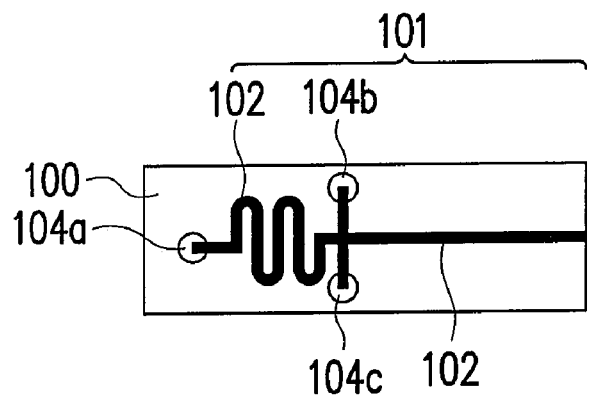
FIGS. 1A-1E are top views showing a manufacturing method of a microfluidic device according to an embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

FIGS. 1A-1E are top views showing a manufacturing method of a microfluidic device according to an embodiment of the present invention. As shown in FIG. 1A, a substrate 100 having at least one device 101 thereon is provided, wherein the device 101 comprises at least one channel 102. In an embodiment, the substrate 100 has a thickness about 0.01~10 mm, preferably in a range of 0.5~2 mm, and has a width and length about 1~5000 μm, preferably in a range of 10-500 μm. The channel 102 of the device 101 may be linear or non-linear, or a portion of the channel 102 is linear and the other portion is non-linear. According to another embodiment, the device 101 formed on the substrate 100 has a plurality of channels 102. The channels 102 may be arranged in array or the like. In addition, the material for the substrate 100 may be polymer, metal, ceramics. For example, the material of the substrate 100 may be plastic, glass or metal alloy. The present invention does not limit the material of the substrate 100, and any material suitable for a bio-chip can be used.

In addition to the channel 102, the device 100 formed on the substrate 100 further comprises other elements, such as reservoirs 104a, 104b, 104c connecting with the channel 102. The reservoirs 104a, 104b, 104c serve sample or reagent loading, waste and the like. In the embodiment, as FIG. 1A shown, one end of the channel 102 is connected with the reservoir 104a, the channel 102 extends toward the edge of the substrate 100, and the other end of the channel 102 is disposed near or at the edge of the substrate 100. According to another embodiment, the device 101 may further comprise reaction chamber(s) (not shown) connecting with the channel 102. The reaction chamber may be polymerase chain reaction (PCR) chamber, purifying chamber or the like. The reaction chamber is designed and arranged depending on the function and use of the device 101. Therefore, the device 101 mainly comprises the channel 102. The design and arrangement of the reaction chamber and reservoir are not limited herein, and the reaction chamber and reservoir are designed based on the use or function of the device 101.

Figure 1B:
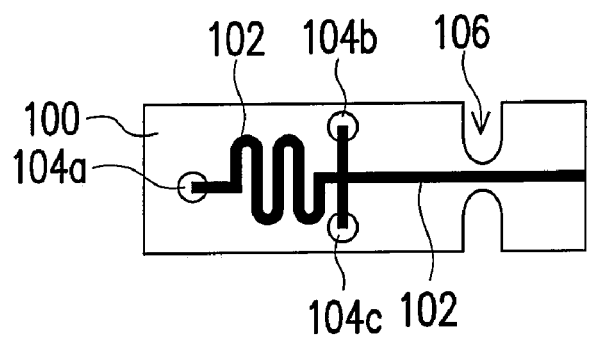

Next, as shown in FIG. 1B, a portion of the substrate 100 in the region 106 is removed. The region 106 is at two sides of the channel 102. The removal step can make the subsequent elongating process more easily, and thus this removal step is optional. The removal step can be performed with cutting, etching or other suitable method.

Figure 1C:
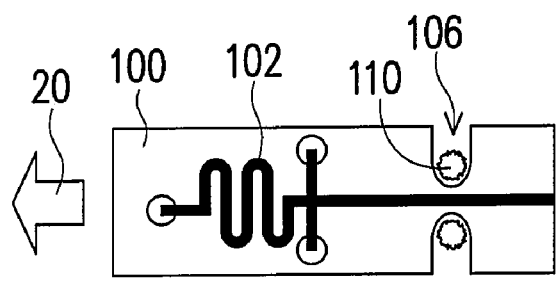
Figure 1D:
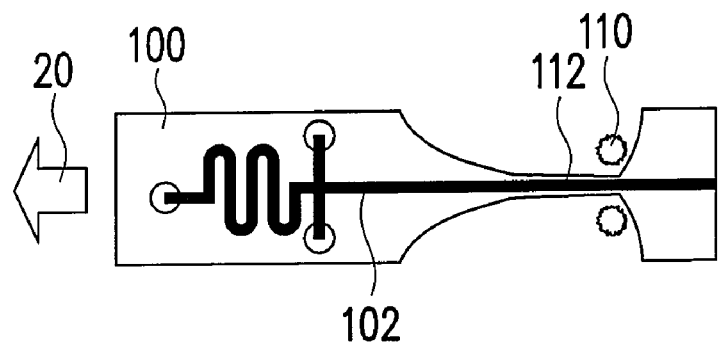

Thereafter, as shown in FIG. 1C, the remained portion at the region 106 is heated, and then the substrate 100 is pulled to elongate the region 106 such that a capillary 112 connected with the channel 102 is formed, shown in FIG. 1D. In an embodiment, the region 106 is heated with a heater 110, such as a resistance heater, a laser heater, a hot air heater, a supersonic heater or the like. In addition, the pulling step for elongating the region 106 to form the capillary 112 is performed by fixing one end of the substrate 100 and pulling the other end of the substrate 100 (as arrow 20 shown). The pulling step can also be performed by pulling two ends of the substrate 100 along two reverse directions.

It should be noted that the region 106 is heated by the heater 110, and the heating temperature is close to or equal to a soften temperature (Ts) of the material of the substrate 100. The soften temperature (Ts) depends on the material of the substrate 100. In details, the region 106 is heated to a temperature higher than 80% Ts and lower than a liquid phase transforming temperature of the material of the substrate 100. For example, if the substrate 100 is made of metal, the region 106 is preferably heated to a temperature lower than a melting point of the metal. In another embodiment, if the substrate 100 is made of a polymer, the region 106 is preferably heated to a temperature lower than a glass transition temperature of the polymer.

Figure 2:
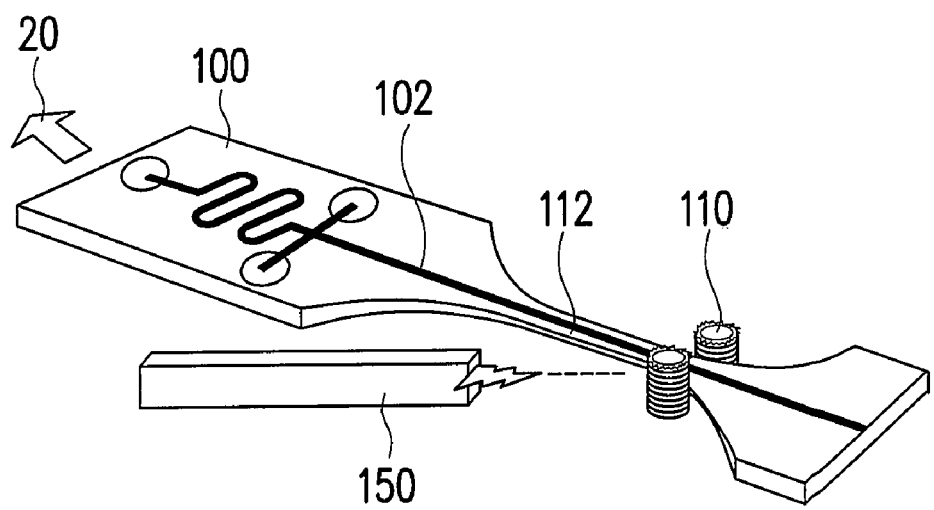
FIG. 2 is a drawing showing a step of performing a temperature measuring step in the manufacturing method of the microfluidic device according to an embodiment of the present invention.

According to another embodiment of the present invention, a temperature measuring step is further performed during the step of heating the region 106, as shown in FIG. 2. In FIG. 2, an infrared thermometer 150 is used to measure the temperature of the heated region 106. The heated region 106 can also be measured by other non-contact type thermometer, a contact type thermometer or a liquid crystal display thermometer. The temperature measuring step can also be carried out to measure the temperatures at the other regions of the substrate 100, if necessary.

Referring to FIGS. 1D and 2, after the pulling step is conducted, the capillary 112 connecting with the channel 102 is formed. In particular, the substrate 100 and the capillary 112 are a unity structure such that the interface between the capillary 112 and the channel 102 is dead-volume free.

Figure 1E:
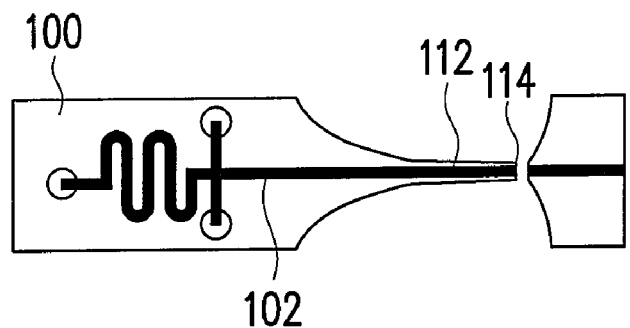

Next, as shown in FIG. 1E, after forming the capillary 112, the capillary 112 can be cut to form an end 114. The end 114 of the capillary 112 may serve as an electrospray tip of a mass spectrometry or a sampling tip. It is noted that the capillary 112 formed in the step of FIG. 1D can be cut or not for different applications.

In the manufacturing method of FIGS. 1A-1E, the substrate 100 having one device 101 thereon and the device 101 having one channel 102 is as an example for illustration, but the present invention does not limit to the substrate having only one device thereon and the device having only one channel. The present invention can also be applied to a substrate having a plurality of devices thereon and each device having at least one channel. The detailed description is shown in FIGS. 3A-3D.

Figure 3A:
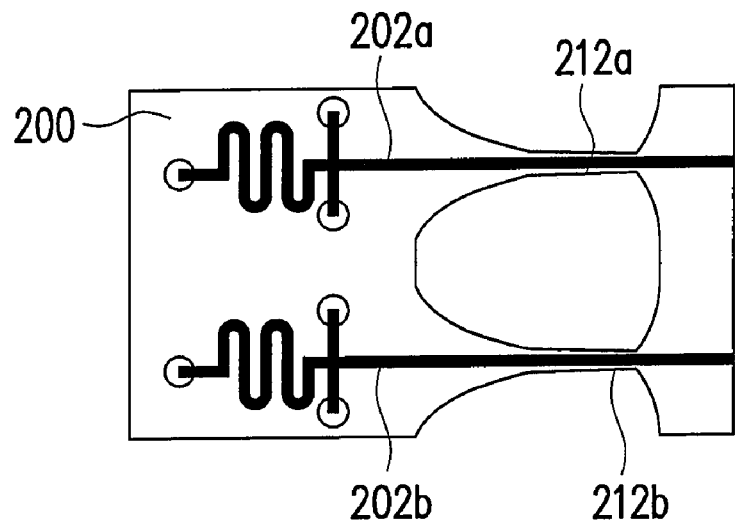
FIGS. 3A-3D are top views showing a manufacturing method of a microfluidic device according to another embodiment of the present invention.

As shown in FIG. 3A, the substrate 200 having two channels 202a, 202b thereon is provided. In addition to the channels 202a, 202b, reaction chambers or reservoirs (not shown) may also be formed on the substrate, if necessary. After the heating and pulling process is performed, two capillaries 212a, 212b respectively connecting with the channels 202a, 202b are formed. The heating and pulling process is the same or similar to that as described above, and thus it is not described again. In the case, the substrate 200 having two channels thereon is as an example for illustration, but it does not limit the present invention. The substrate 200 may have more than two channels thereon, and the number of the formed capillaries is not limited either.

Figure 3B:
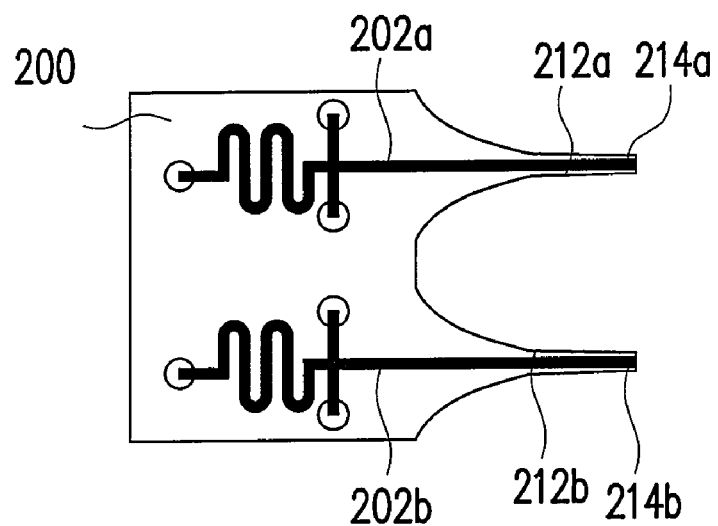

As shown in FIG. 3B, after forming the capillaries 212a, 212b, the capillaries 212a, 212b can be cut to form ends 214a, 214b, and the ends 214a, 214b may serve as electrospray tips or sampling tips. Similarly, the capillaries 212a, 212b can be cut or not for different applications.

Figure 3C:
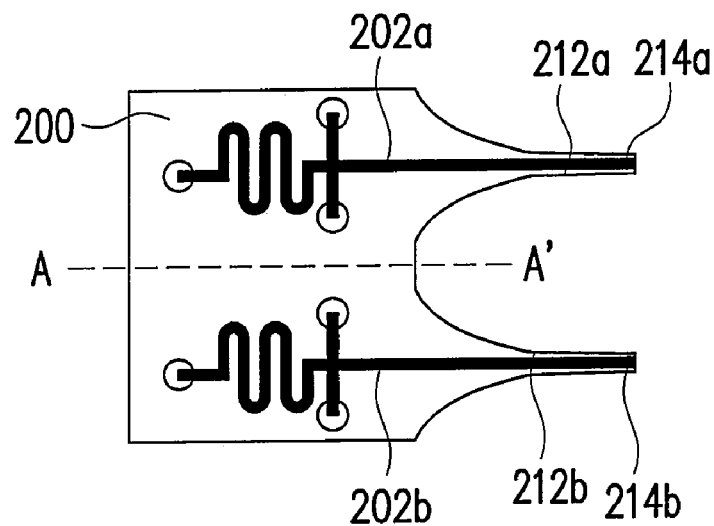
Figure 3D:
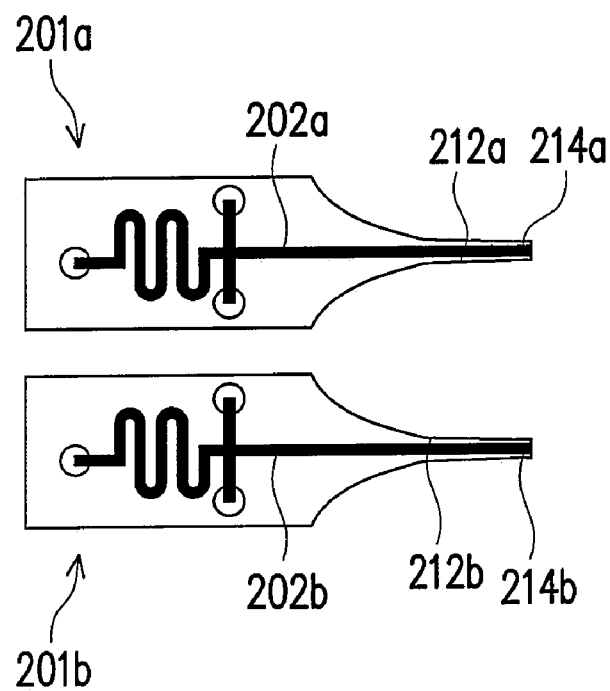

Moreover, according to another embodiment of the present invention, as shown in FIG. 3C, after forming the capillaries 212a, 212b, a cutting step along the dotted line A-A' may be performed, so as to form two separate chip devices 201a, 201b shown in FIG. 3D. Also, according to another embodiment, two or more channels on the substrate may be as a chip unit, such that after cutting the substrate, there are a plurality of channels and a plurality of capillaries on a single chip device.

Figure 4A:
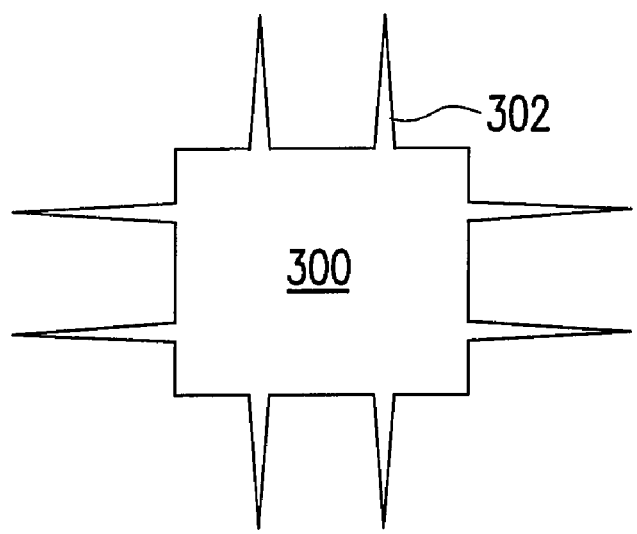
FIG. 4A is a top view of a microfluidic device according to another embodiment of the present invention.

In another embodiment, the formed capillaries may be arranged in array. As shown in FIG. 4A, the substrate 300 has a plurality channels and relative elements (not shown) thereon, and a plurality of capillaries 302 are formed at the edge of the substrate 300. In addition, the substrate 300 may also be cut to form a plurality of chip devices.

Figure 4B:
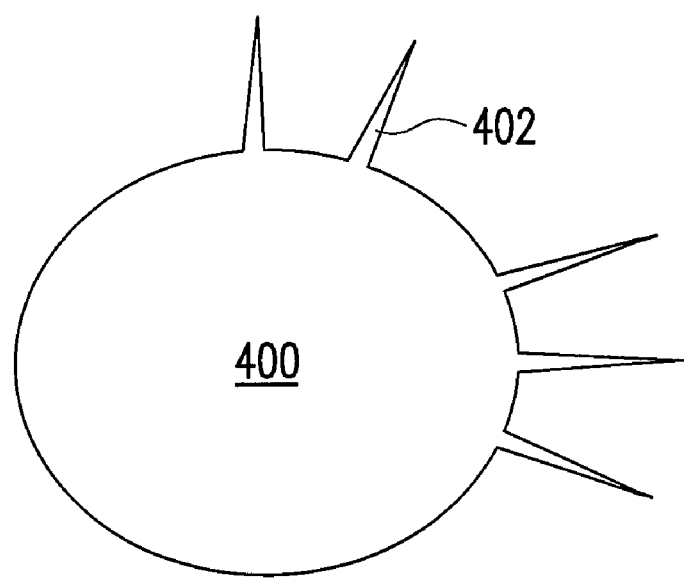
FIG. 4B is a top view of a microfluidic device according to another embodiment of the present invention.

In the embodiments as above mentioned, the substrate is a rectangular substrate for illustration. However, the shape of the substrate is not limited herein. The substrate can also be other shape, such as circular shape. As shown in FIG. 4B, the substrate 400 has a plurality channels and relative elements thereon, and a plurality of capillaries 402 are formed at the edge of the substrate 400. Also, the substrate 400 may be cut to form a plurality of chip devices.

Figure 5:
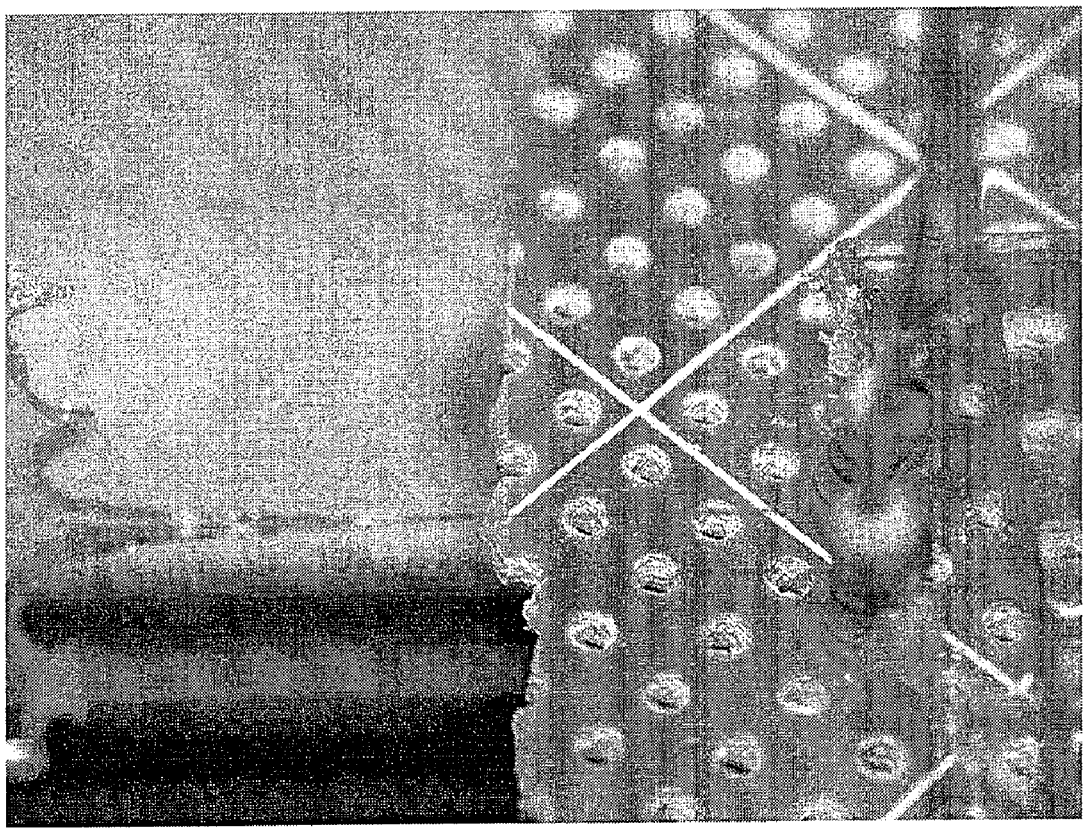
FIG. 5 is a picture showing a capillary of a microfluidic device according to an embodiment of the present invention.

FIG. 5 is a picture showing a microfluidic device with a capillary according to an embodiment of the present invention. The left part of FIG. 5 is a portion of the substrate and a capillary is successfully formed after the heating and pulling step. In particular, the formed capillary and the substrate are a unity structure.

Figure 6:
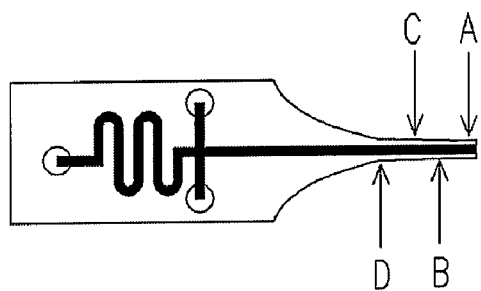
FIG. 6 is a picture showing different portions of a capillary of a microfluidic device according to an embodiment of the present invention.
Figure 6:
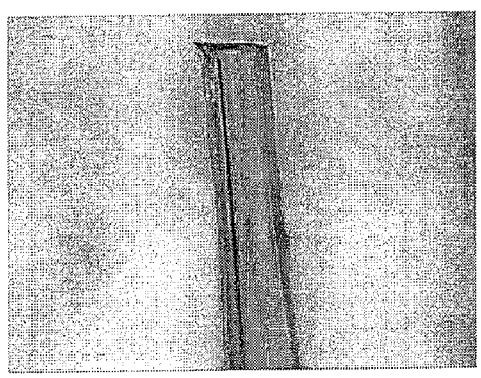
Figure 6:
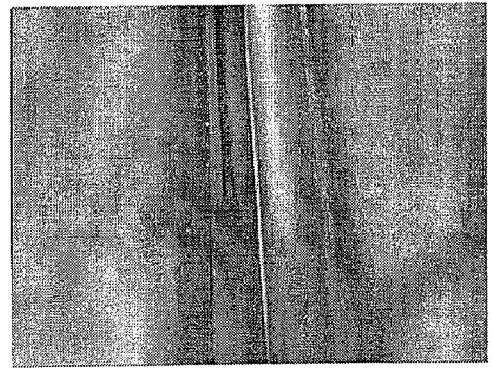
Figure 6:
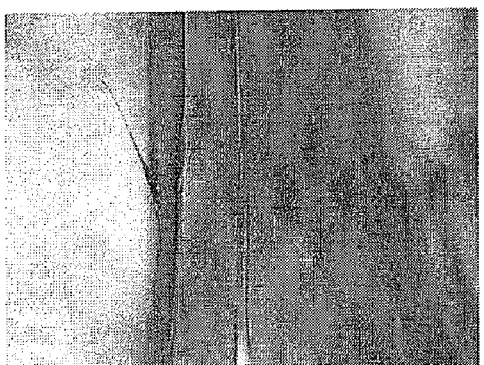
Figure 6:
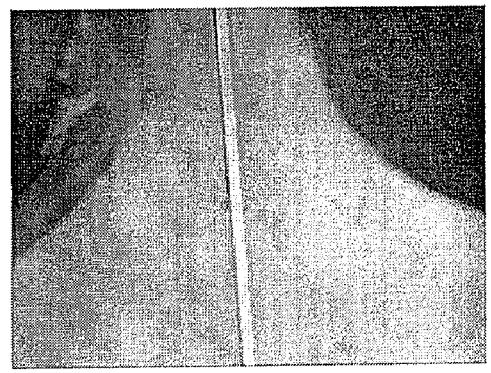

FIG. 6 is a picture showing different portions of a capillary of a microfluidic device according to an embodiment of the present invention. Referring to FIG. 6, the A portion is the end of the capillary and the B, C, and D are the portions sequentially far away the end of the capillary. As the picture of the D portion shown, the capillary is connected with the channel, and the capillary and the substrate are a unity structure, such that the interface between the capillary and the channel is dead-volume free.

Figure 7A:
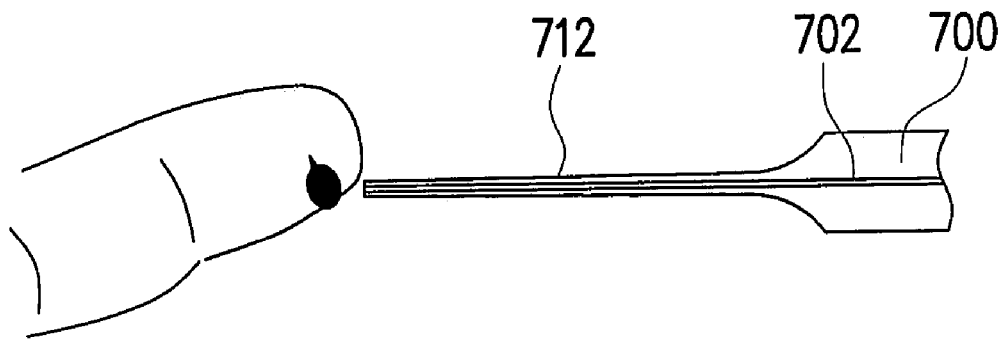
FIGS. 7A-7B are drawings showing using the capillary of the microfluidic device as a sampling tip.
Figure 7B:
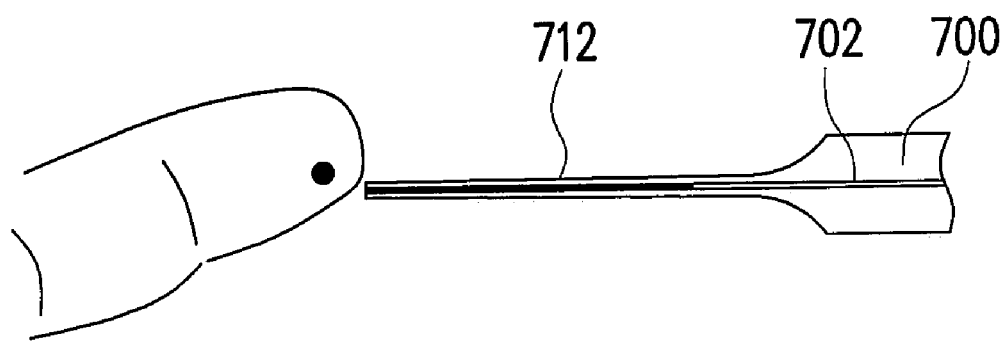

FIGS. 7A-7B are drawings showing using the capillary of the microfluidic device as a sampling tip. As shown in FIGS. 7A-7B, the substrate 700 has a channel 702 and relative elements (not shown) thereon, and a capillary 712 is formed at the edge of the substrate 700. The capillary 712 can be used as a sampling tip for loading a sample, such as blood sample, urine sample or other liquid or gas sample. The sample can be drawn by capillary force or an addition force, such as a syringe or internal vacuum device.

Figure 8:
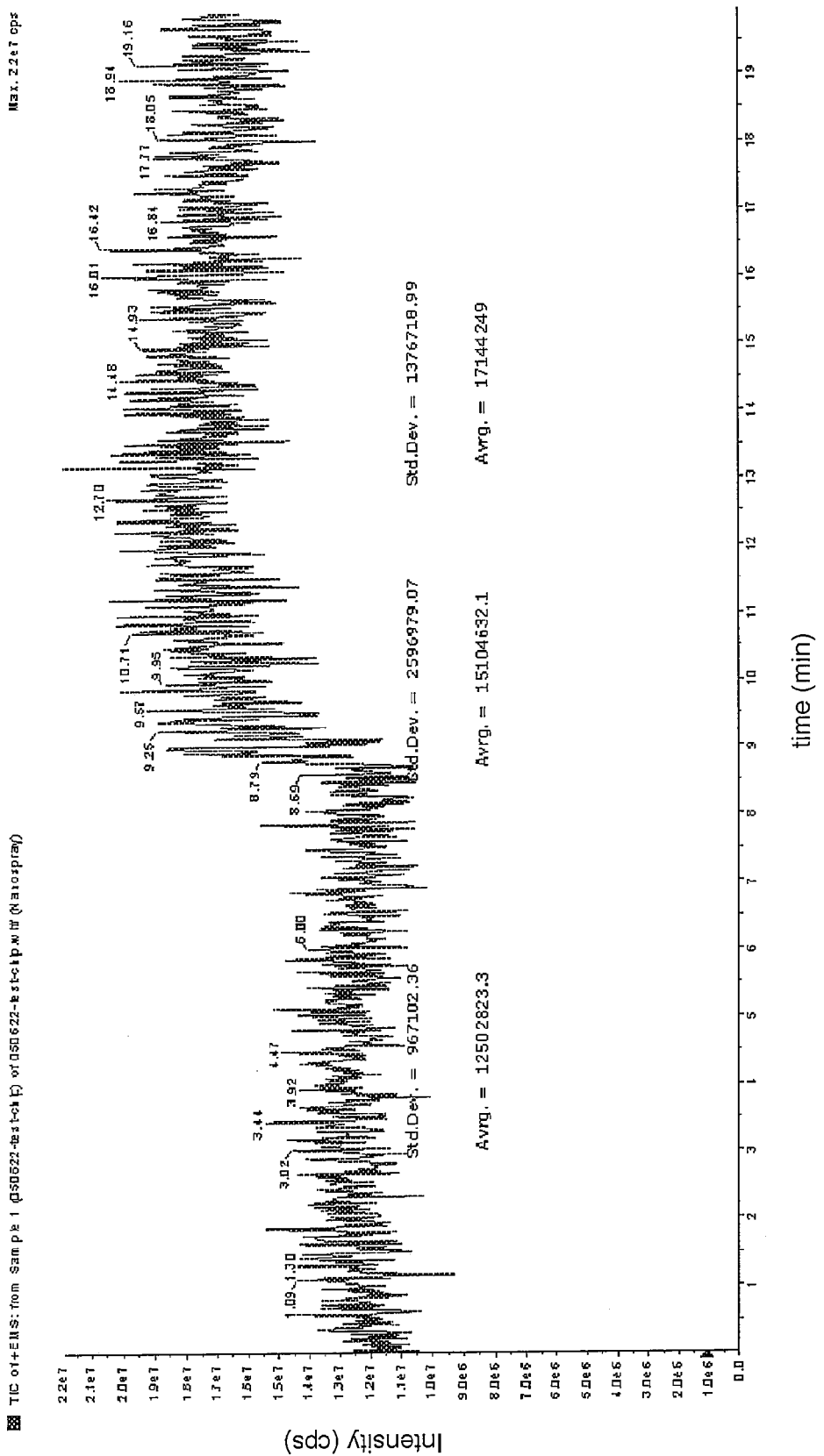
FIG. 8 is a mass spectrometry diagram which obtained from a microfluidic device having a capillary as an electrospray tip fabricated by the method of the present invention.

The capillary of the microfluidic device can also be used as the electrospray tip of a mass spectrometry instrument. FIG. 8 shows a mass spectrometry data of the microfluidic device according to an embodiment of the present invention. In the Example of FIG. 8, the loaded sample is 50% acetonitrile, and the mass spectrometry instrument is MDS SCIEX 4000 Q TRAP™ LC/MS/MS (manufactured by Applied Biosystem). In the mass spectrometry data of FIG. 8, the electrospray intensity is in a range of 1~2E7 cps, the stability from 1 to 9 minutes is 7.73% and the stability from 9 to 20 minutes is 8.03%. Therefore, using the capillary of the microfluidic device of the embodiment as the electrospray tip has good stability.

According to another embodiment, the microfluidic device can be designed to have two or more capillaries, wherein one of the capillaries is used as the sampling tip and the other one of the capillaries is used as the electrospray tip. If this microfluidic device is manufactured, a sample can be loaded by using the sampling tip. Then, the sample would flow through the channel and may perform reactions in the reaction chamber. Next, the sample will be analyzed through the electrospray tip. In the embodiment, the capillary of the microfluidic device is used as an electrospray tip or/and sampling tip. However, it does not limit the present invention. The capillary of the microfluidic device can also be used as other tips.

For the foregoing, the capillary of the microfluidic device and the substrate are a unity structure such that the interface between the capillary and the channel is dead-volume free. In addition, the capillary of the microfluidic device is formed with a heating and pulling step, and thus the method for forming the capillary is simple, fast and low cost, and it is easy to mass produce.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of manufacturing a microfluidic device, comprising:
   providing a substrate having at least one device thereon, wherein the device comprises at least one channel;
   removing a portion of the substrate beside the channel to form a recesses region;
   depositing a heating device at the recessed region to heat the substrate at the recessed region; and
   continuously heating the substrate at the recessed region and pulling the substrate to elongate the substrate at the recessed region such that at least one capillary connecting with the channel is formed.

2. The method of claim 1, wherein:
   the substrate has a plurality of devices thereon, and each of the devices comprises at least one channel; and
   after pulling the substrate, a plurality of capillaries are formed, wherein each channel is connected with at least one of the capillaries.

3. The method of claim 2, wherein the channels are arranged in array and the formed capillaries are also arranged in array.

4. The method of claim 2, further comprising performing a cutting step to the substrate so as to form a plurality of chip devices, wherein each device chip has at least one channel and at least one capillary.

5. The method of claim 1, wherein the step of heating the region beside the channel is performed with a resistance heater, a laser heater, a hot air heater or a supersonic heater.

6. The method of claim 1, wherein the region is heated to a temperature higher than a 80% soften temperature (80% Ts) of the substrate and lower than a liquid phase transforming temperature of the substrate.

7. The method of claim 1, further comprising removing a portion of the substrate beside the channel before heating the region.

8. The method of claim 1, further comprising cutting the capillary to form an end after the capillary is formed.

9. The method of claim 1, wherein the step of pulling the substrate to elongate to form the capillary connecting with the channel comprises fixing one end of the substrate and pulling another end of the substrate so as to form the capillary, or pulling two ends of the substrate along two reverse directions so as to form the capillary.

10. The method of claim 1, further comprising measuring the temperature of the region during the step of heating the region beside the channel.

11. The method of claim 10, wherein the step of measuring the temperature of the region is performed with an infrared thermometer, a contact type thermometer or a liquid crystal display thermometer.

12. The method of claim 1, wherein the substrate has a thickness in a range of 0.01~10 mm and has a width and a length in a range of 1~5000 μm.

13. The method of claim 1, wherein the material of the substrate comprises polymer, metal or ceramics.

14. A microfluidic device, comprising:
a substrate having a top surface, a bottom surface and at least one side surface connecting with the top surface and the bottom surface, wherein the substrate has a plurality of devices on the top surface, and each device has at least one channel extending to the side surface of the substrate; and
a plurality of capillaries, each capillary connecting with one of the channels and protruding out of the substrate from the side surface of the substrate, wherein the substrate and the capillaries are a unity structure such that the interface between the capillaries and the channels is dead-volume free.

15. The microfluidic device of claim 14, wherein the substrate has a plurality of devices thereon, and each of the devices has at least one channel connecting with at least one capillary.

16. The microfluidic device of claim 15, wherein the channels are arranged in array and the capillaries are also arranged in array.

17. The microfluidic device of claim 14, wherein the substrate has a thickness in a range of 0.01~10 mm and has a width and a length in a range of 1~5000 μm.

18. The microfluidic device of claim 14, wherein the material of the substrate comprises polymer, metal or ceramics.

19. The microfluidic device of claim 14, wherein the device further comprises at least one reservoir connecting with the channel of the device.

20. The microfluidic device of claim 14, wherein the capillary is used as an electrospray tip or a sampling tip.

* * * * *